(12) United States Patent
Shi

(10) Patent No.: US 7,322,997 B2
(45) Date of Patent: Jan. 29, 2008

(54) AUTOMATIC SAFE DISPOSABLE BLOOD SAMPLING DEVICE OF CASING SELF-LOCKING TYPE

(76) Inventor: Guoping Shi, No. 32, Xinlian Road, Pingjiang, Suzhou City (CN) 215008

( * ) Notice: Subject to any disclaimer, the term of this patent is extended or adjusted under 35 U.S.C. 154(b) by 339 days.

(21) Appl. No.: 11/018,532

(22) Filed: Dec. 21, 2004

(65) Prior Publication Data

US 2005/0234487 A1    Oct. 20, 2005

(30) Foreign Application Priority Data

Apr. 16, 2004    (CN) .................. 2004 2 0026368 U

(51) Int. Cl.
*A61B 17/32* (2006.01)
(52) U.S. Cl. ...................... 606/181; 606/167; 606/182; 600/583
(58) Field of Classification Search ............... 606/167, 606/170, 172, 181–185; 600/583
See application file for complete search history.

(56) References Cited

U.S. PATENT DOCUMENTS 6,053,930 A * 4/2000 Ruppert ...................... 606/181
6,136,013 A * 10/2000 Marshall et al. ............ 606/167

FOREIGN PATENT DOCUMENTS

| CN | 2486104 Y | 4/2002 |
| CN | 24286104 Y * | 4/2002 |
| CN | 200420025752.5 | 3/2005 |

* cited by examiner

*Primary Examiner*—Glenn K. Dawson
*Assistant Examiner*—Kathleen Sonnett
(74) *Attorney, Agent, or Firm*—Madson & Austin

(57) ABSTRACT

An automatic safe disposable blood sampling device includes a casing with a launching chamber formed therein. The launching chamber has a lancet needle-exiting hole at a front end thereof; a lancet needle arranged inside the launching chamber; a spring; a launching mechanism composed of the spring and a catch-launching mechanism; a press-launching mechanism provided on the casing; and a self-locking mechanism composed of barbs provided on the press-launching mechanism and self-locking hooks or notches provided on the casing which engage corresponding barbs. When pressed, the press-launching mechanism triggers the catch-launching mechanism, to disengage the lancet needle from the casing. The spring pushes the lancet needle so as to launch the lancet needle. During forward movement of the press-launching mechanism, the barbs pass across the self-locking hooks or notches. In the process of retraction, the barbs are locked with the self-locking hooks or notches and cannot return to their initial states.

4 Claims, 3 Drawing Sheets

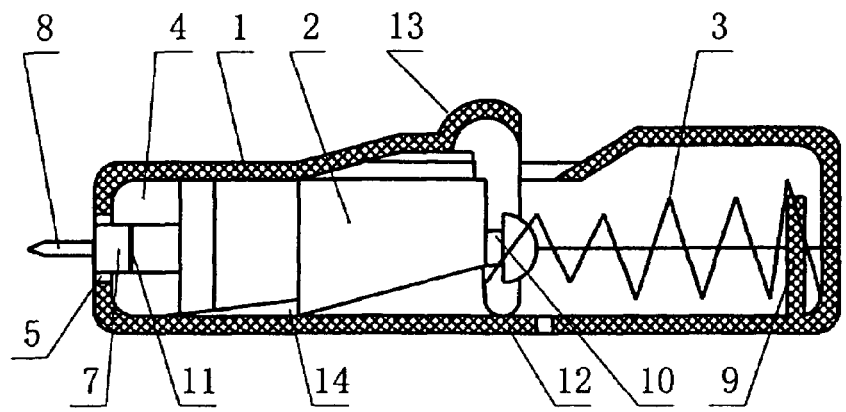
Fig.4
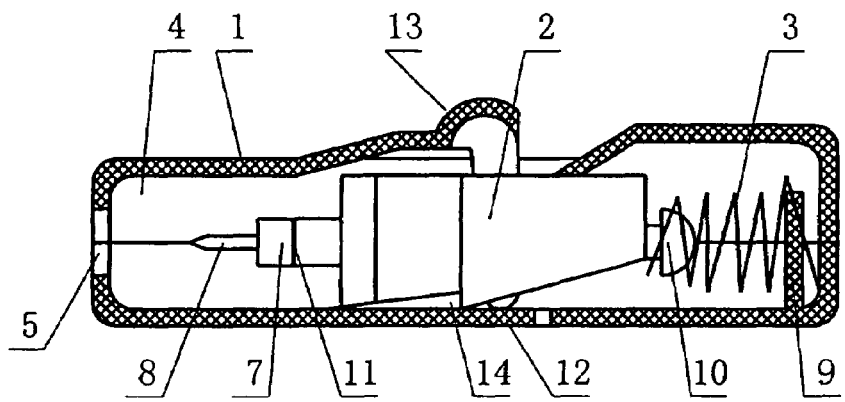
Fig.5
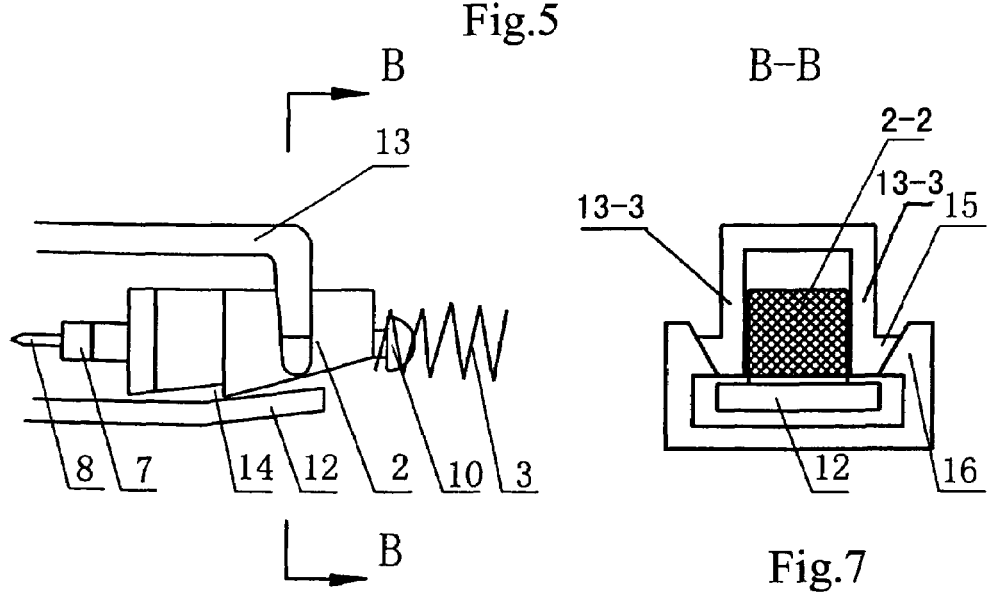
Fig.6
Fig.7

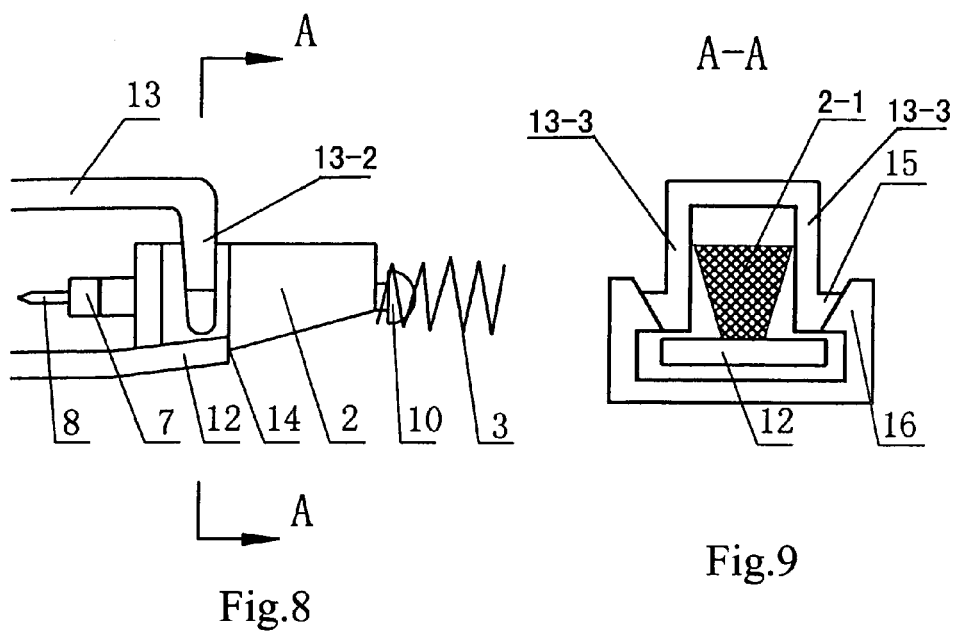
Fig.8
Fig.9
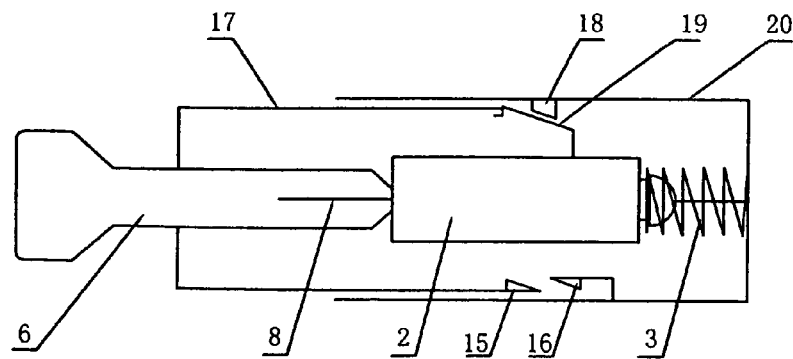
Fig.10

AUTOMATIC SAFE DISPOSABLE BLOOD SAMPLING DEVICE OF CASING SELF-LOCKING TYPE

BACKGROUND OF THE INVENTION

The present invention generally relates to an automatic safe disposable blood sampling device for medical use, more particularly, to a casing self-locking type of automatic safe blood sampling device, in which a press button of which is locked by engagement thereof with the casing of the blood sampling device after a lancet needle of the blood sampling device is launched so that the blood sample device is brought into a self-locking state and can not be reused.

Various types of medical blood sampling device are known, there is a tendency to develop a "mini" type automatic blood sampling device which is safe and disposable once the lancet needle is launched. In order to make it disposable, this kind of blood sampling device is provided with a disposable self-locking mechanism which achieves self-locking effect immediately after a lancet needle of the blood sampling device is launched, thus causing the catch-launching mechanism failure. Therefore, the potential safety hazards involved in the previous blood sampling device are thoroughly eliminated.

Presently, there are two types of self-locking mechanism. The first type of self-locking mechanism employs a structure in which the lancet needle is engaged with a casing, that is, the lancet needle and the casing each are provided with a special structure, the engagement of the lancet needle with the casing achieves a self-locking effect after the lancet needle of the blood sampling device is launched. For example, the Chinese Utility Model No. CN2486104Y filed on Jul. 30, 2001 and granted to the applicant of the present application on Apr. 17, 2002 discloses an automatic safe disposable blood sampling device having a new type catch-launching mechanism, in the blood sampling device of the above Chinese Utility Model No. CN2486104Y, an elastic arm C is slantwise provided on the lancet needle and a stopping notch is provided in the casing of the blood sampling device. After the lancet needle of blood sampling device is launched, the elastic arm C is retracted together with the lancet needle so as to fall into the stopping notch to be self-locked therewith.

The second type of self-locking mechanism is a lancet needle self-locking structure, that is, the self-locking mechanism is completely provided on the lancet needle, and achieves a self-locking effect after the lancet needle of the blood sampling device is launched. For example, the Chinese Patent Application No. 200420025752.5 filed on Mar. 25, 2004 by the same applicant as that of the present application discloses an automatic safe disposable blood sampling device of lancet needle self-locking type. In the blood sampling device, and an elastic arm is provided on a side portion of the lancet needle. A self-locking hook is provided on an end of the elastic arm, and the elastic arm is inwardly bent upon application of an external force when the lancet needle of the blood sampling device is launched by pressing. Consequently, and the end is forced across the hook so as to be caught by the self-locking hook, thus achieving the self-locking effect. The above two types of self-locking mechanisms have disadvantageous in their structures, features and effects respectively.

BRIEF SUMMARY OF THE INVENTION

An object of the present invention is to provide a novel casing self-locking type of automatic safe blood sampling device based on "one-off launching and not reusable" principle, in the casing self-locking type of automatic safe blood sampling device of the present invention, a self-locking mechanism is completely formed by structures on a casing. This self-locking mechanism is of the third type, that is, the casing self-locking type.

In order to achieve the above object, there is provided a casing self-locking type of automatic safe blood sampling device, comprising: a casing formed with a launching chamber therein, the launching chamber being provided with a lancet needle-exiting hole at a front end thereof; a lancet needle arranged inside the launching chamber; a spring; a launching mechanism composed of the spring and a catch-launching mechanism; a press-launching mechanism provided on the casing; and a self-locking mechanism composed of barbs provided on the press-launching mechanism and self-locking hooks or self-locking notches provided on the casing corresponding to the barbs, the self-locking hooks or self-locking notches being located on paths along which the barbs are advanced, respectively.

The related contents and variations of the above technical scheme are explained as follows:

1. In the above technical scheme, the self-locking mechanism has two types, i.e. the side-pressing type and the end-pressing type.

2. With regard to the side-pressing type of self-locking mechanism, the press-launching mechanism is embodied as press button for launching provided on a side of the blood sampling device, the press button is mounted on a side of a casing or formed by a first elastic arm extended integrally from the side of the casing, barbs are provided on the press button, and self-locking hooks or self-locking notches are provided on the casing corresponding to the barbs.

3. With regard to the end-pressing type of self-locking mechanism, the press-launching mechanism is embodied as a sliding sleeve provided at an end of the blood sampling device, the sliding sleeve as a part of the casing of the blood sampling device is slideably connected to another part of the casing, barbs are provided on the sliding sleeve, and self-locking hooks or self-locking notches are provided on provided on the another part of the casing corresponding to the barbs respectively.

The operation of the blood sampling device according to the present invention is described as follows.

When being pressed, the press-launching mechanism triggers the catch-launching mechanism, so that the lancet needle is disengaged from the casing, the spring pushes the lancet needle so as to launch the lancet needle. As the same time, because of movement of the press-launching mechanism, the barbs pass across the self-locking hooks or self-locking notches during the forward movement thereof. Therefore, during retraction, the barbs are locked with the self-locking hooks or self-locking notches and thereby can not return to their primed states, thereby the catch-launching mechanism is caused to be failure and can not be reused.

By comparison to the prior art, the blood sampling device has the following advantages.

1. The self-locking mechanism of the blood sampling device according to the present invention is novel, the self-locking function is achieved by changing structure of the casing, so that the blood sampling device is simple in structure and can be operated reliably.

2. The operation of the self-locking mechanism is performed in the following orders: the self-locking mechanism firstly enters into its self-locking state, and then enters into launching state. However, the conventional self-locking mechanism using engagement of the lancet needle with the casing is firstly launched, and then enters into its self-locking state. Therefore, the blood sampling device according to the present invention can reflect the design philosophy of one-off launching and not reusable.

3. In comparison to the conventional self-locking mechanism, the self-locking mechanism of the present invention is novel, simple in structure.

4. The blood sampling device according to the present invention is easy to use and simple to operate.

5. After use, the lancet needle is retracted into the casing automatically and will be not exposed to outside, thus ensuring safety of the used blood sampling device.

BRIEF DESCRIPTION OF THE DRAWINGS

FIG. 4 is a structural sectional view of the blood sampling device according to the first embodiment of the present invention, showing that the blood sampling device is in a launching state;

FIG. 5 is a structural sectional view of the blood sampling device according to the first embodiment of the present invention, showing a state after use;

FIG. 6 is a partial sectional view of a self-locking mechanism of the blood sampling device according to the first embodiment of the present invention, showing a state before the lancet needle is locked;

FIG. 7 is a sectional view taken along line B-B in FIG. 6;

FIG. 8 is a partial sectional view of a self-locking mechanism of the blood sampling device according to the first embodiment of the present invention, showing that the blood sampling device is in a state to be launched;

FIG. 9 is a sectional view taken along line A-A in FIG. 8; and

FIG. 10 is a structural schematic view of the blood sampling device according to the second embodiment of the present invention.

Figure 1:
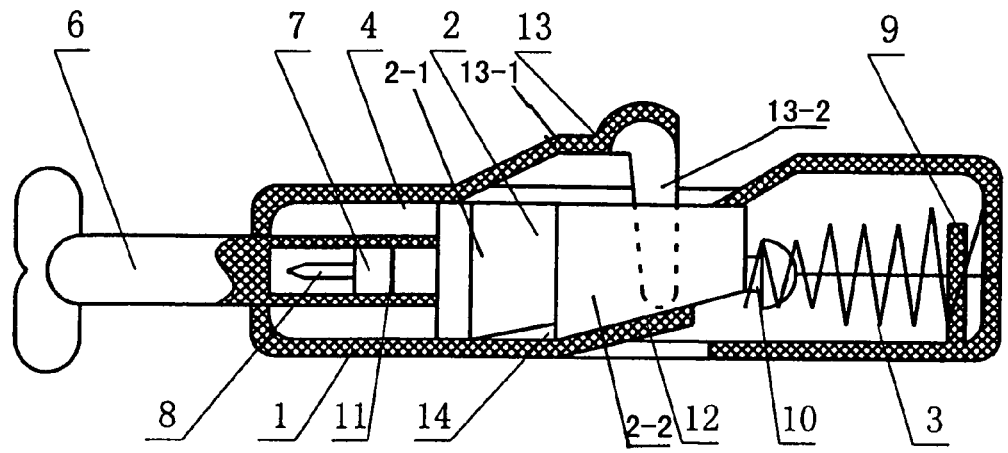
FIG. 1 is a structural sectional view of the blood sampling device according to the first embodiment of the present invention, showing an assembled state before use.
Figure 2:
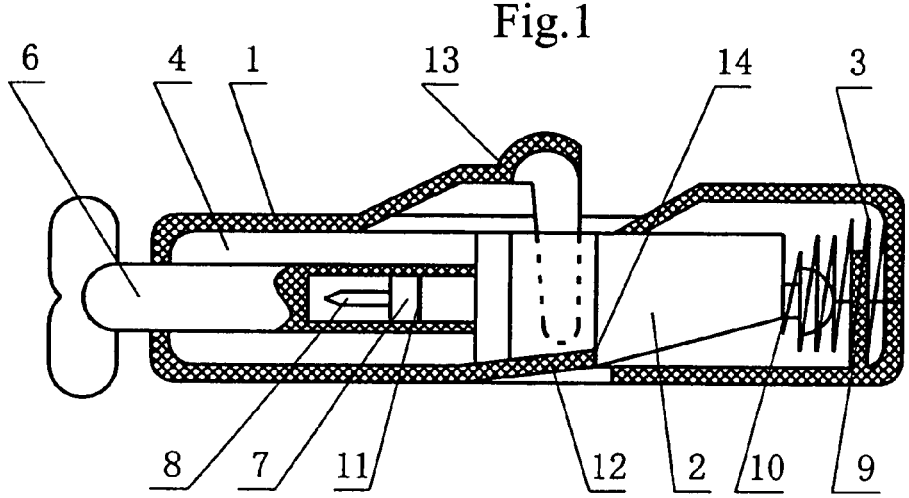
FIG. 2 is a structural sectional view of the blood sampling device according to the first embodiment of the present invention, showing that the lancet needle is pushed into a self-locked state.
Figure 3:
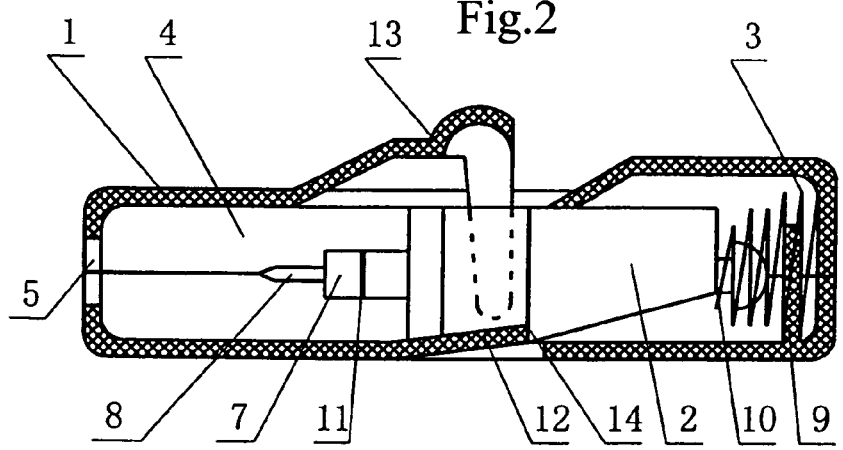
FIG. 3 is a structural sectional view of the blood sampling device according to the first embodiment of the present invention, showing that the blood sampling device is in a state to be launched with a lancet needle cap being removed.

In the above drawings, the reference numerals denote the following members respectively: 1: case; 2: lancet needle; 2-1: first locking section; 2-2: second locking section; 3: spring; 4: launching chamber; 5: lancet needle-exiting hole; 6: elongated lancet needle cap; 7: boss; 8: lancet needle tip; 9: catching plate; 10: catching groove; 11: protruding ring; 12: second elastic arm; 13: first elastic arm; 13-1: intermediate section of the first elastic arm; 13-2: extension section of the first elastic arm; 13-3: leg; 14: blocking notch; 15: barb; 16: self-locking hook; 17: sliding sleeve; 18: bevel; 19: elastic catching member; 20: outer sleeve.

DETAILED DESCRIPTION OF THE INVENTION

Embodiments of the present invention will be described in detail with reference to the accompanying drawings.

THE FIRST EMBODIMENT

As shown in FIG. 1 to FIG. 5, there is illustrated a side-pressing and casing self-locking type of automatic safe disposable blood sampling device, comprising a casing 1, a lancet needle 2, an elongated lancet needle cap 6 and a spring 3.

The casing 1 comprises an upper part and a lower part which are connected into an integral structure by using holes and pins provided on contacting surfaces thereof respectively. A launching chamber 4 is formed inside the casing 1, and the lancet needle 2 and the spring 3 are arranged in the launching chamber 4. The spring 3 is located behind the lancet needle 2 wherein the head of the spring 3 is caught in a catching groove 10, and the tail of the spring 3 is caught on the catching plate 9, thus forming an elastic sliding structure in a launching direction. A lancet needle-exiting hole 5 is provided at one end of the casing 1 in a direction consistent with the launching chamber direction. A cylindrical boss 7 is provided at the head of the lancet needle 2, and a lancet needle tip 8 is extended centrally out of the boss 7. Further, a protruding ring 11 is provided circumferentially on the boss 7. An elongated lancet needle cap 6 has a rod structure and is provided with a deep hole in a front portion thereof and a tail wing at a rear end thereof. The front portion of the elongated lancet needle cap 6 passes through the lancet needle-exiting hole 5 so as to fit over the boss 7, and the elongated lancet needle cap 6 can be prevented from retracting accidentally from the boss 7 through engagement of the protruding ring 11 with the deep hole.

A catch-launching mechanism and a self-locking mechanism are provided between the lancet needle 2 and a side of the casing 1 along a compression path of the spring 3.

As shown FIGS. 6 to 9, the catch-launching mechanism comprises a second elastic arm 12 extended from a side of the casing 1, a first elastic arm 13 extended from another side of the casing 1, and a blocking notch 14 provided in the lancet needle 2. The second elastic arm 12 and the blocking notch 14 are located at a bottom side of the casing 1 in FIGS. 1 to 5, and the second elastic arm 12 is inclined towards to the inside of the launching chamber 4. A cantilever end of the second elastic arm 12 is engaged with the blocking notch 14 so as to form a locking structure. The first elastic arm 13 serving as a press button is located at an upper side of the casing 1 in FIG. 1, and an intermediate section 13-1 of the first elastic arm 13 serving as a pressing portion protrudes from the upper side of the casing 1 in FIG. 1. An extension section 13-2 of the first elastic arm 13 has an inversed U-shape, and the lancet needle 12 is located between two legs 13-3 of the inversed U-shape extension section 13-2 while two legs 13-3 extend into holes provided on the casing 1 and pass across the launching chamber 4 respectively. Distal ends of the two legs 13-3 contact or are close to the cantilever end of the second elastic arm 12.

The self-locking mechanism comprises barbs 15 provided respectively on two outer sides of the inversed U-shape extension section 13-2, and self-locking hooks 16 provided at positions corresponding to the barbs 15 on the inner wall of the casing 1. The self-locking hooks 16 are located on paths along which the barbs 15 are advanced. In order to protect the self-locking mechanism in a state in which the lancet needle 2 of the blood sampling device is not launched, the lancet needle 2 is provided with a first locking section 2-1 and a second locking section 2-2. Prior to being locked, the position of the second locking section 2-2 corresponds to that of the inversed U-shape extension section 13-2 as shown in FIG. 1, and the bottom side of the second locking section 2-2 has the same inclination and inclined direction as that of the second elastic arm 12. The cross section of the second locking section 2-2 has substantially the same width from top to bottom, and widths of gaps formed between the two sides of the second locking section 2-2 and the inner walls of the casing 1 are smaller than that of the two legs 13-3 of the inversed U-shape extension section 13-2. Therefore, at this time, the inversed U-shape extension section 13-2 of the first elastic arm 13 can not move downwards. As a result, the barbs 15 on the inversed U-shape extension section 13-2 can not engage with the self-locking hooks 16 on the casing 1 so as to lock with each other respectively, as shown in FIG. 7. When the lancet needle 2 is pushed towards to the rear side (right side in FIG. 1) of the casing 1, the first locking section 2-1 of the lancet needle 2 is moved rearwards so that the position of the first locking section 2-1 is brought to gradually come close to the position of the inversed U-shape extension section 13-2 of the first elastic arm 13. The width of the cross-section of the first locking section 2-1 is decreased gradually from top to bottom, and the widths of gaps formed between two sides of the first locking section 2-1 and the inner walls of the casing 1 are equal to or larger than that of the two legs 13-3 of the inversed U-shape extension section 13-2 respectively. Therefore, the inversed U-shape extension section 13-2 can be moved downwards so that the barbs 15 can be moved downwards along with the inversed U-shape extension section 13-2 so as to be engaged and locked with the self-locking hooks 16 on the casing 1. Before the cantilever end of the second elastic arm 12 is caught by the blocking notch, since the second locking section 2-2 has a larger width in the transverse direction of the cross-section thereof (the cross-section of the second locking section 2-2 has a rectangle shape in the embodiment, as shown in FIG. 7), the inversed U-shape extension section 13-2 of the first elastic arm 13 can not pass through the gaps formed between the inversed U-shape extension section 13-2 and inner walls of the casing 1 even if pressing the inversed U-shape extension section 13-2, thus achieving the self-locking mechanism. The lancet needle 2 is brought into a locking state by pushing the elongated lancet needle cap 6, at this time, the first locking section 2-1 of the lancet needle 2 corresponds to the inversed U-shape extension section 13-2, since the transverse width of the cross-section of the first locking section 2-1 is decreased from top to bottom (the cross-section of the first locking section 2-1 has a tapered shape in this embodiment, as shown in FIG. 9), the widths of the gaps increase, so that two legs 13-3 of the inversed U-shape extension section 13-2 of the first elastic arm 13 can be inserted into the gaps formed between the inversed U-shape extension section 13-2 and inner walls of the casing 1 by pressing the inversed U-shape extension section 13-2, contact with and act on the cantilever end of the second elastic arm 12 at last, thus causing the cantilever end of the second elastic arm 12 to disengage from the blocking notch 14.

THE SECOND EMBODIMENT

As shown in FIG. 10, there is illustrated an end-pressing and casing self-locking type of automatic safe disposable blood sampling device, comprising a casing, a lancet needle 2, an elongated lancet needle cap 6 and a spring 3. The casing comprises a sliding sleeve 17 and an outer sleeve 20, and an elastic catching member 19 is provided at a side of the lancet needle 2. When the elongated lancet needle cap 6 is pushed, the lancet needle 2 presses the spring 3. While the elastic catching member 19 is caught at an end of the sliding sleeve 17, thus achieving locking. The self-locking mechanism comprises a barb 15 and a self-locking hook 16, and the barb 15 is provided on the sliding sleeve 17 while the self-locking hook 16 is provided on the outer sleeve 20.

In operation, the elongated lancet needle cap 6 is first pulled out, then the outer sleeve 20 is held by hand of a user. Thereafter, the lancet needle-exiting hole in the casing is directed at a region of a human body to be blood-sampled and the blood sampling device is pressed. At the same time, the sliding sleeve 17 is moved by an external force towards a closed end (right end in FIG. 10) of the outer sleeve 20 (rightward in the FIG. 10) inside an inner chamber formed inside the outer sleeve 20. The bevel 18 forces the elastic catching member 19 to disengage from the sliding sleeve 17, and the spring 3 pushes the lancet needle 2 along a guide groove (not shown) to launch the lancet needle 2. Then a lancet needle tip of the lancet needle 2 is ejected out of the lancet needle-exiting hole so as to puncture the region of a human body to be blood-sampled. At the same time, since the sliding sleeve 17 is slid towards the closed end of the outer sleeve 20 inside inner chamber of the outer sleeve 20, the barb 15 is engaged and locked with the self-locking hook 16. Therefore, the sliding sleeve 17 can not further slide inside the inner chamber of the outer sleeve 20, thus causing the blood sampling device to fail.

While the present invention has been described with reference to the specific embodiments thereof, it should be understood by those ordinary skilled in the art that various changes may be made and equivalents may be substituted without departing from the true spirit and scope of the invention. In addition, many modifications may be made to adapt to a particular situation, material, composition of matter, process, process step or steps, to the objective, spirit and scope of the present invention. All such modifications are intended to be within the scope of the claims appended hereto.

The invention claimed is:

1. A casing self-locking type of automatic safe blood sampling device, comprising:
   a casing formed with a launching chamber therein, the launching chamber being provided with a lancet needle-exiting hole at a front end thereof;
   a lancet needle arranged inside the launching chamber;
   a spring;
   a launching mechanism composed of the spring and a catch-launching mechanism;
   a press-launching mechanism provided on the casing; and
   a self-locking mechanism composed of barbs provided on the press-launching mechanism and self-locking hooks or self-locking notches provided on the casing corresponding to the barbs, the self-locking hooks or self-locking notches being located on paths along which the barbs are advanced, respectively, wherein the press-launching mechanism is configured to be a press button for launching which is provided on a side of the blood sampling device, and the press button being formed into a first elastic arm mounted on or extended integrally from a side of the casing, and wherein the barbs are provided on the press button and the self-locking hooks or self-locking notches being provided on the casing at positions corresponding to those of the barbs, respectively, wherein:

the catch-launching mechanism comprises a second elastic arm extended from the casing, the first elastic arm, and a blocking notch formed in the lancet needle, wherein:

the second elastic arm and the blocking notch are located on one same side of the casing;

the second elastic arm is inclined towards inside of the launching chamber;

a cantilever end of the second elastic arm can be engaged with the blocking notch so as to form a locking structure; and the first elastic arm is located on the other side of the casing and functioned as the press button for launching;

an extension section of the first elastic arm passes across the launching chamber so as to contact or be close to the cantilever end of the second elastic arm;

the barbs are provided on the extension section of the first elastic arm; and the self-locking hooks or self-locking notches are provided on an inner wall of the casing at positions corresponding to those of the barbs, respectively.

2. The blood sampling device according to the claim 1, wherein:

the extension section of the first elastic arm has an inversed U-shape, the lancet needle is located between two legs of the inversed U-shape extension section, distal ends of the two legs are brought into contact with or come close to the cantilever end of the second elastic arm, the barbs are provided on outer sides of the two legs and the self-locking hooks or self-locking notches are provided on an inner wall of the casing at positions corresponding to those of the barbs, respectively.

3. The blood sampling device according to the claim 2, further comprising:

an elongated lancet needle cap which is fitted over a front portion of the lancet needle and extends out of the needle-exiting hole, wherein the lancet needle has a first locking section and a second locking section, a bottom side of the second locking section is inclined in a direction along which the second elastic arm is inclined, a cross-section of the second locking section has substantially the same width from top to bottom, widths of the gaps formed between two sides of the second locking section and the inner wall of the casing respectively are smaller than that of the two legs of the inversed U-shape extension section, so that when the position of the second locking section corresponds to that of the inversed U-shape extension section, the inversed U-shape extension section can not be moved downwards so as to engage and lock with the self-locking hooks on the inner wall of the casing; width of a cross-section of the first locking section is smaller than that of the cross-section of the second locking section and widths of the gaps formed between two sides of the first locking section and the inner wall of the casing respectively are smaller than that of the two legs of the inversed U-shape extension section, so that when the position of the first locking section is corresponding to that of the inversed U-shape extension section, the inversed U-shape extension section can be moved downwards so as to engage and lock with the self-locking hooks on the inner wall of the casing.

4. The blood sampling device according to the claim 1, wherein:

the press-launching mechanism is formed into a sliding sleeve provided on one end of the blood sampling device, the sliding sleeve is a part of the casing and slid over another part of the casing, the barbs are provided on the sliding sleeve and the self-locking hooks or self-locking notches are provided on the casing at positions corresponding to those of the barbs.

* * * * *